United States Patent [19]

Elam

[11] 4,341,210
[45] * Jul. 27, 1982

[54] CUFFED ENDOTRACHEAL TUBE AND METHOD

[76] Inventor: James O. Elam, 6723 S. Euclid Ave., Chicago, Ill. 60649

[*] Notice: The portion of the term of this patent subsequent to Nov. 25, 1997, has been disclaimed.

[21] Appl. No.: 157,735

[22] Filed: Jun. 30, 1980

Related U.S. Application Data

[63] Continuation of Ser. No. 942,854, Sep. 15, 1978, Pat. No. 4,235,239, which is a continuation-in-part of Ser. No. 800,420, May 25, 1978, abandoned.

[51] Int. Cl.³ ............................................. A61M 25/00
[52] U.S. Cl. ............................ 128/207.15; 128/349 B
[58] Field of Search ...................... 128/207.14, 207.15, 128/207.16, 207.17, 207.18, 10, 344, 349 B

[56] References Cited

U.S. PATENT DOCUMENTS

| | | | |
|---|---|---|---|
| 3,889,688 | 6/1975 | Eamkaow | 128/207.15 |
| 3,915,173 | 10/1975 | Brekke | 128/207.15 |
| 4,090,518 | 5/1978 | Elam | 128/207.15 |
| 4,091,816 | 5/1978 | Elam | 128/207.15 |
| 4,233,984 | 11/1980 | Walling | 128/207.14 |
| 4,235,239 | 11/1980 | Elam | 128/207.15 |
| 4,248,221 | 2/1981 | Winnard | 128/207.15 |

Primary Examiner—Henry J. Recla
Attorney, Agent, or Firm—Arnstein, Gluck & Lehr

[57] ABSTRACT

A cuffed endotracheal tube and method designed for insertion of the tube through the mouth of a patient to provide a passage for artificial respiration. The device includes an elongated flexible air tube having proximal and distal end portions. A pair of enlargements encircle the tube intermediate the proximal and distal end portions. The lower of the enlargements is sized and shaped to fall short of fully occupying the cavity defined by the wall of the trachea and rests at or below the opening defined by the lower lateral surfaces of the larynx. The upper of the enlargements is sized and shaped to fully occupy the cavity defined by the wall of the pharynx and seals the opening defined by the superglottic structure of the glottis. At least the upper of the enlargements is an inelastic inflatable-deflatable cuff secured to the tube proximal to the lower of the enlargements. The device further includes separate inflation means for each cuff permitting the cuff to be inflated independently of any other cuff. A method for using the endotracheal tube provides a safe and effective way of assuring proper placement by providing a positive external indication by reason of the location of the upper and lower enlargements on either side of the glottis so that the tube is anchored sufficiently to withstand inadvertent extubation.

9 Claims, 10 Drawing Figures

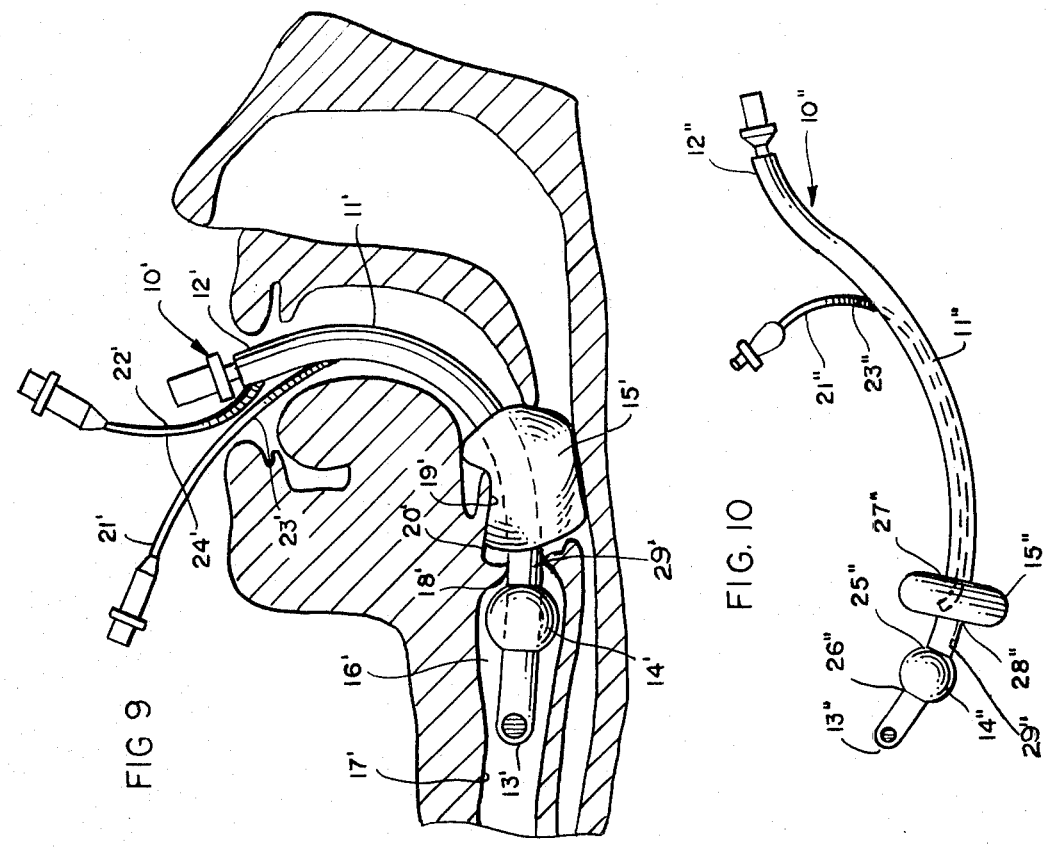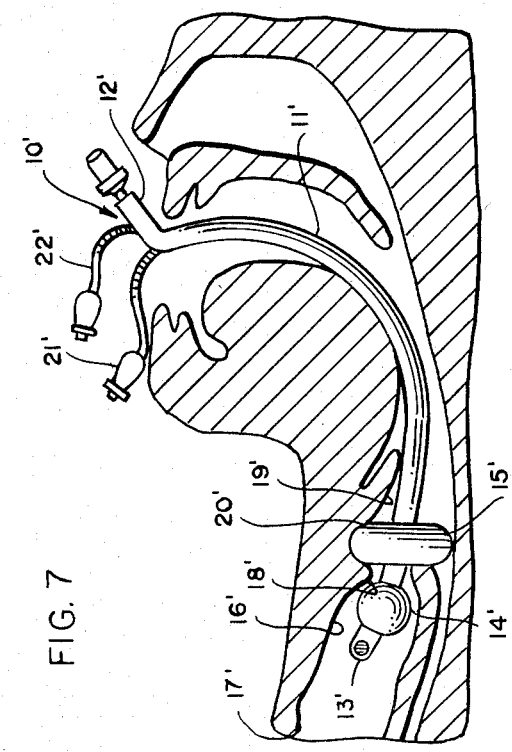

CUFFED ENDOTRACHEAL TUBE AND METHOD

This is a continuation application of application Ser. No. 942,854, filed Sept. 15, 1978, now U.S. Pat. No. 4,235,239, which was a continuation-in-part application of Ser. No. 800,420, filed May 25, 1978, now abandoned.

BACKGROUND OF THE INVENTION

This invention relates to endotracheal airway devices and, more particularly, to a cuffed endotracheal tube and method.

Conventionally, the cuff of a single cuffed endotracheal tube is inflated with air following insertion of the device into the middle portion of the trachea of a patient to achieve an air-tight seal of the space between the tube and surrounding tracheal wall. As such, the single cuffed endotracheal tube has been routinely employed for many decades to prevent upper airway obstruction and to facilitate artificial respiration of the unconscious or anesthesized patient. However, recent investigations have disclosed several defects in the design of conventional single cuffed endotracheal tubes.

Among these defects are, firstly, the failure to prevent secretions from accumulating in the upper trachea; secondly, the abrading of the vocal cords as a result of to and fro motion caused by respiration; and thirdly, the injury to the cilia and surface membranes of the mid-trachea caused by intra-cuff sealing pressure upon the tracheal wall.

While all of these defects are significant, the possible injury to the cilia and surface membranes of the mid-trachea is perhaps most damaging. The degree of such injury is proportional to the magnitude of lateral wall-cuff pressure in excess of 15 centimeters of water and to the duration such pressure is applied. Conventionally, the single cuffed endotracheal tube has been used with the cuff inflated in place in the mid-trachea several centimeters below the larynx where compression of the ciliated endothelium of the trachea causes the injury.

Conventional single cuffed endotracheal tubes produce a non-leak seal in the mid-trachea at pressures which occlude the blood perfusion of the tracheal mucosa after a period of time producing tissue necrosis without sufficient assurances against bronchial intubation and inadvertent extubation. This also holds true for alternately inflated midtracheal double cuff structures forming a part of the prior art. In contrast, the present invention provides a pair of enlargements at least one of which is an inelastic inflatable-deflatable cuff, anchoring the tube on either side of the larynx at pressures lower than those sufficient to cause injury in a manner preventing bronchial intubation and inadvertent extubation.

Another problem arising from prevailing practices of tracheal intubation is the failure of the conventional single cuffed endotracheal tube to prevent secretions from passing through an unprotected space between the vocal cords and the tube. The result is accumulation of a ring of contaminated material in the upper trachea above the single inflated cuff which enters the lung when the cuff is deflated at extubation and which can be even more immediate with alternately inflated mid-tracheal double cuff structures. During intubation, this residue or ring of infected secretions trickles into the larynx and becomes entrapped above the single inflated cuff until subsequent extubation allows the ring of secretions to enter the mid-trachea where injured cilia fail to protect the lung.

The normal protective mechanism by which the cilia carry the secretions upward in the respiratory tree until reflex coughing results in their removal fail to operate. My invention eliminates such aspiration by virtue of placing an inelastic inflatable-deflatable cuff above the larynx to keep the upper airway secretions from entering the laryngeal area. After insertion and initial inflation, the cuff rests above the larynx thereby preventing exposure of the larynx and trachea to contamination.

By leaving inflated the cuff described herein, oral secretions may be removed by suction catheter with both the larynx and trachea protected. Thus, the present invention is superior to the conventional single cuffed endotracheal tubes as well as the alternately inflated mid-tracheal double cuff structure in at least four important features, as herein embodied, including (1) a positive means of anchoring a pair of enlargements on either side of the vocal cords thereby preventing tube motion, accidental extubation, or further penetration of the tube into a bronchus, (2) the option of zero sealing pressure below the vocal cords, (3) the prevention of secretions from traveling into the area of the upper trachea or larynx where they might cause permanent injury, and (4) a method of using a cuffed endotracheal tube providing a positive external indication by reason of the location of the enlargements on either side of the glottis. While the prior art has attempted to deal with the problems associated with endotracheal airway devices in various ways and with various degrees of success, the present invention represents an important advance in the art.

SUMMARY OF THE INVENTION

The present invention relates to a cuffed endotracheal tube and method designed for insertion of the tube through the mouth of a patient to provide a passage for artificial respiration. The device includes an elongated flexible air tube having proximal and distal end portions. A pair of enlargements encircle the tube intermediate the proximal and distal end portions. The lower of the enlargements is sized and shaped to fall short of fully occupying the cavity defined by the wall of the trachea and rests at or below the opening defined by the lower lateral surfaces of the larynx. The upper of the enlargements is sized and shaped to fully occupy the cavity defined by the wall of the pharynx and seals the opening defined by the superglottic structure of the glottis. At least the upper of the enlargements is an inelastic inflatable-deflatable cuff secured to the tube proximal to the lower of the enlargements. The device further includes separate inflation means for each cuff permitting the cuff to be inflated independently of any other cuff.

In one embodiment, the upper and lower enlargements are both inelastic inflatable-deflatable cuffs and the separate inflation means are two distinct channels within the wall of the tube leading from the cuffs to the proximal end portion of the tube for syringe attachment. The cuffs have proximal and distal end portions as well with the distal end portion of the upper of the cuffs being positioned near the proximal end portion of the lower of the cuffs. A cuff segment intermediate the lower and upper of the cuffs and in communication with one of the cuffs can also be provided having a generally triangular configuration under full inflation and being sized and shaped to fully occupy and seal the opening defined by the glottis.

In another embodiment, the upper enlargement is an inelastic inflatable-deflatable cuff but the lower enlargement is a bulbous segment of the flexible air tube itself and the inflation means is a single channel within the wall of the tube leading from the cuff to the proximal end portion of the tube for syringe attachment. The cuff and the bulbous segment have proximal and distal end portions as well with the distal end portion of the cuff being positioned near the proximal end portion of the bulbous segment. A cuff segment intermediate the bulbous segment and the cuff and in communication with the cuff can also be provided having a generally triangular configuration under full inflation and being sized and shaped to fully occupy and seal the opening defined by the glottis.

The method for using the cuffed endotracheal tubes of the type described includes a unique combination of steps. First, an elongated flexible air tube is provided having proximal and distal end portions wherein a pair of enlargements, at least the upper one of which is an inelastic inflatable-deflatable cuff, encircle the tube intermediate the proximal and distal end portions thereof. Second, the tube is inserted through the mouth of a patient into the trachea to provide a passage for artificial respiration with the cuff deflated until the lower enlargement is positioned below the subglottic structure of the glottis. Third, the lower enlargement is sized and shaped to fall short of fully occupying the cavity defined by the wall of the trachea but is sized greater than the opening defined by the lower lateral surfaces of the larynx. Fourth, the tube is withdrawn causing the lower enlargement to move upwardly in the trachea until resistance is encountered indicating that the lower enlargement is positioned against the opening defined by the lower lateral surfaces of the larynx. Fifth, the cuff is inflated to a size and shape fully occupying the cavity defined by the superglottic structure of the glottis and to a size greater than the opening defined by the superglottic structure of the glottis. Sixth, the tube is moved toward insertion through the mouth of the patient further into the trachea with the cuff inflated such that resistance indicates that the cuff is properly anchored in the opening defined by the glottis and the lower enlargement rests at or below the opening defined by the lower lateral surfaces of the larynx. With these featues, the method provides a safe and effective way of assuring proper placement of an endotracheal airway device by providing a positive external indication by reason of the location of the enlargements on either side of the glottis.

The present invention is therefore directed to a cuffed endotracheal tube and method capable of overcoming all of the problems heretofore encountered in the use of such devices. It is an object of the present invention to provide an elongated flexible air tube having proximal and distal end portions wherein a pair of enlargements, at least the upper one of which is an inelastic inflatable-deflatable cuff, encircle the tube intermediate the proximal and distal end portions with separate inflation means being provided for inflating each cuff independently of any other cuff. The provision of the structure and the realization of the advantages to be derived therefrom constitute additional important objects of the present invention with still other objects to be appreciated from a consideration of the details of construction and operation set forth in the accompanying specification, claims and drawings.

BRIEF DESCRIPTION OF THE DRAWINGS

The invention is described in conjunction with the accompanying drawings, in which

FIG. 7 is a partially cross-sectional, partially schematic view of still another embodiment of the cuffed endotracheal tube of the invention installed in a patient with a pair of cuffs inflated and resting above and below the larynx with the lower cuffs resting below the opening defined by the lower lateral surfaces of the larynx;

FIG. 8 is a view similar to FIG. 7 but with the endotracheal tube removed from the patient;

FIG. 9 is a view similar to FIG. 7 illustrating an optional construction; and

FIG. 10 is a schematic view of a still further embodiment of the cuffed endotracheal tube of the invention with an upper inelastic inflatable-deflatable cuff and a lower bulbous segment forming a pair of enlargements encircling the tube.

DESCRIPTION OF THE PREFERRED EMBODIMENT

Figure 1:
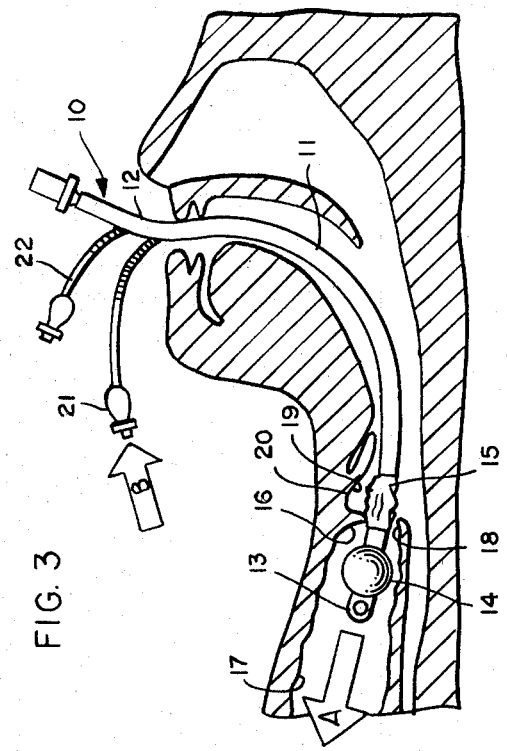
FIG. 1 is a partially cross-sectional, partially schematic view of an embodiment of the cuffed endotracheal tube of the invention installed in a patient with a pair of cuffs inflated and resting above and below the larynx with the lower cuff resting at the opening defined by the lower lateral surfaces of the larynx.

In the illustration given and with reference first to FIG. 1, the head of a patient is shown in schematic cross-section with the reference numeral 10 generally designating a cuffed endotracheal tube in accordance with the present invention. The device 10 includes an elongated flexible air tube 11 having proximal and distal end portions 12 and 13, respectively. A pair of enlargements 14 and 15 encircle the tube 11 intermediate the proximal and distal end portions 12 and 13. The lower of the enlargements 14 is sized and shaped to fall short of fully occupying the cavity 16 defined by the wall 17 of the trachea and rests at the opening 18 partially defined by the lower lateral surfaces of the larynx. The upper of the enlargements 15 is sized and shaped to fully occupy the cavity 19 defined by the wall 20 of the pharynx and seals the opening 18 partially defined by the superglottic structure of the glottis. At least the upper of the enlargements 15 is an inelastic inflatable-deflatable cuff secured to the tube 11 proximal to the lower of the enlargements 14. The device further includes separate inflation means (such as 21) for inflating each cuff (such as 14) independent of any other cuff. With these features of construction, the endotracheal airway device 10 is well suited for insertion through the mouth of a patient to provide a passage for artificial respiration.

Figure 2:
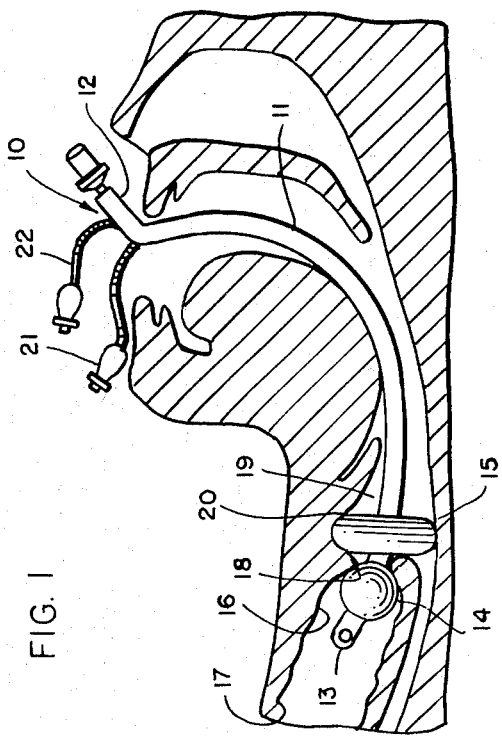
FIG. 2 is a view similar to FIG. 1 but with the cuffed endotracheal tube removed from the patient.
Figure 5:
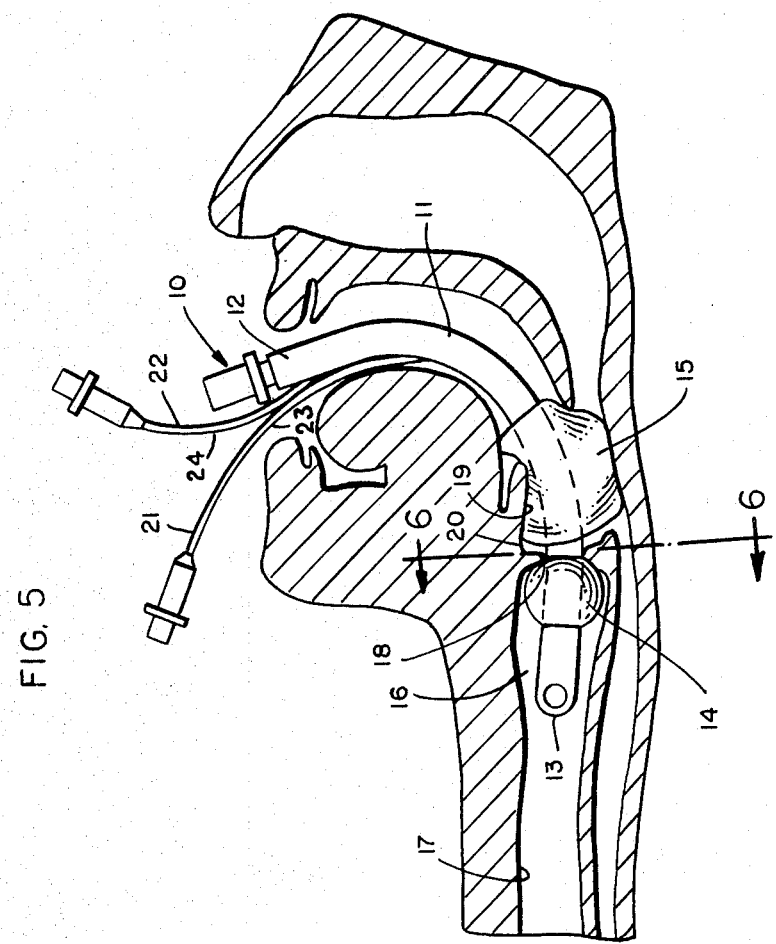
FIG. 5 is a partially cross-sectional, partially schematic view of another embodiment of the cuffed endotracheal tube of the invention installed in a patient with a pair of cuffs inflated and resting above and below the larynx with an intermediate cuff segment of generally triangular configuration.
Figure 6:
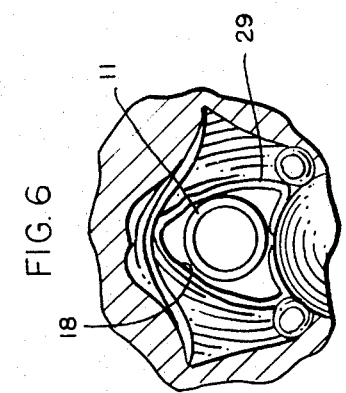
FIG. 6 is a cross-sectional view taken on the line 6—6 of FIG. 5 illustrating the triangular intermediate cuff segment.

Referring to FIG. 2, the cuffed endotracheal tube 10 can be understood in greater detail. It will be seen that the lower of the enlargements 14 in this embodiment is also an inelastic inflatable-deflatable cuff secured to the tube 11 distal to the upper cuff 15. The device 10 then will include separate inflation means 21 and 22 in the form of first and second distinct channels 23 and 24, respectively, within the wall of the tube 11 and leading from the cuffs 14 and 15, respectively, to the proximal end portion 12 for syringe attachment. The connectors are conventional and will, therefore, not be discussed since they do not form a part of the present invention. The cuff 14, which is preferably a thickwalled generally spherical member, has proximal and distal end portions 25 and 26, respectively. It generally approximates with slight contact the semi-rigid structure of the lower glottis where damage to body tissue is most likely to occur. The cuff 15, which is preferably a thin-walled doughnut-shaped member wider than it is long, has proximal and distal end portions 27 and 28, respectively, with the distal end portion 28 of the upper of the cuffs 15 being positioned near the proximal end portion 25 of the lower of the cuffs 14. It seals against the soft tissues of the lower pharynx and upper glottis where damage to body tissue is least likely to occur. The spacing between the proximal end portion 25 and the distal end portion 28 is sufficient to accommodate the glottis although they can actually be contiguous so long as the geometric configuration of the cuffs 14 and 15 under full inflation so permits. Furthermore, a cuff segment 29 can be provided intermediate the cuffs 14 and 15, respectively, in communication with one of the cuffs and having a generally triangular configuration (as shown in FIGS. 5 and 6) under full inflation being sized and shaped to fully occupy and seal the opening 18 defined by the glottis.

The cuffs 14 and 15 are preferably constructed of a material having inelastic properties such as polyvinylchloride (PVC). It will be seen from the drawings that when both cuffs 14 and 15 are inflated they form together a dumbbell-like shape in appearance. The lower of the cuffs 14 is preferably thick-walled with the upper of the cuffs 15 being thin-walled. It will be appreciated that the inelastic nature of the cuffs 14 and 15 as well as the specific shaping, sizing and thickness make it possible to inflate them so they locate on either side of the glottis. With these features of construction, a leaktight pneumatic system is provided which makes it virtually certain to avoid injury in the trachea.

The upper of the cuffs 15 is designed so as to accommodate a higher pressure than the lower of the cuffs 14 without risk of injury to the wall 20 of the pharynx. This can be done since the pharynx is freely movable and tolerates expansion making it possible to size and shape the upper of the cuffs 15 so as to seal under full inflation the opening 18 partially defined by the superglottic structure of the glottis. This also makes it possible to design the lower of the cuffs 14 so as to rest under full inflation at the opening 18 partially defined by the lower lateral surfaces of the larynx. As a result, the lower of the cuffs 14 can be sized and shaped to fall short of fully occupying the cavity 16 defined by the wall 17 of the trachea to act only as an anchor against inadvertent extubation rather than a seal (as also shown in an alternative embodiment in FIGS. 7-9 discussed in detail hereinafter) thereby precluding injury to the cilia and surface membranes of the mid-trachea that might otherwise be caused by intra-cuff sealing pressure upon the tracheal wall.

By virtue of the spacing of the cuffs 14 and 15 and their geometrical configuration, the device 10 is anchored in use to prevent bronchial intubation or inadvertent extubation. This can be done at pressures lower than those sufficient to cause injury. It is therefore possible to anchor the device 10 without occluding the blood perfusion of the tracheal mucosa which would, after a period of time, produce tissue necrosis. It is also possible to obtain a positive external indication that the cuffs 14 and 15 are located on either side of the glottis. This can be accomplished because the device 10 will, in that event, be properly anchored in place. In contrast, the device 10 could easily be withdrawn or further inserted in the event that it had inadvertently been lodged in the esophagus.

The cuffed endotracheal tube 10 also prevents secretions from entering the trachea. The secretions may be removed from the pharynx by suction catheter prior to collapse of the upper of the cuffs 15. This prevents the secretions from being aspirated into the trachea at the time of extubation. The introduction of a suction catheter into the esophagus displaces the upper of the cuffs 15 slightly in order for the catheter tip to enter the esophagus. At such time, the pressure in the upper of the cuffs 15 protects the trachea from secretion contamination since it seals the opening 18 partially defined by the superglottic structure of the glottis.

Referring to FIGS. 7 and 8, an alternative embodiment of cuffed endotracheal tube 10' is illustrated. It will be appreciated that the cuffed endotracheal tube 10' is very similar to the cuffed endotracheal tube 10 described in detail hereinabove. The only difference between the two embodiments of cuffed endotracheal tubes is that the proximal end portion 25' of the lower of the cuffs 14' is spaced further from the distal end portion 28' of the upper of the cuffs 15' than are the corresponding enlargements or cuffs 14 and 15. It will be appreciated thata the cuffed endotracheal tube 10' and the cuffed endotracheal tube 10 are identical in every other respect. With this sole distinction, the lower of the cuffs 14' can be designed so as to rest under full inflation below the opening 18' defined by the lower lateral surfaces of the larynx.

Accordingly, the lower of the cuffs 14' can again be sized and shaped to fall short of fully occupying the cavity 16' defined by the wall 17' of the trachea to act only as an anchor against inadvertent extubation thereby precluding injury to the cilia and surface membranes of the mid-trachea that might otherwise be caused by intra-cuff sealing pressure upon the tracheal wall. However, the spacing between the proximal end portion 25' of the lower of the cuffs 14' and the distal end portion 28' of the upper of the cuffs 15' is sufficient in this embodiment not only to accommodate the glottis but also to permit the lower of the cuffs 14' to rest without contacting the opening 18' defined by the lower lateral surfaces of the larynx. Moreover, a cuff segment 29' can again be provided intermediate the cuffs 14' and 15', respectively, (as shown in FIG. 9 and similar to cuff segment 29 illustrated in FIGS. 5 and 6) in communication with one of the cuffs and having a generally triangular configuration under full inflation being sized and shaped to fully occupy and seal the opening 18' defined by the glottis.

By virtue of the spacing of the cuffs 14' and 15' and their geometrical configuration, the device 10' is again anchored in use to prevent bronchial intubation or inadvertent extubation. This can be done at pressures lower than those sufficient to cause injury. It is therefore possible to again anchor the device 10' without occluding the blood prefusion of the tracheal mucosa which would, after a period of time, produce tissue necrosis. It is also possible to again obtain a positive external indication that the cuffs 14' and 15' are located on either side of the glottis. This can be accomplished because the device 10' will, in that event, be properly anchored in place. In contrast, the device 10' could again easily be withdrawn or further inserted in the event that it had inadvertently been lodged in the esophagus.

The cuffed endotracheal tube 10' also prevents secretions from entering the trachea. The secretions may be removed from the pharynx by suction catheter prior to the collapse of the upper of the cuffs 15'. This prevents the secretions from being aspirated into the trachea at the time of extubation. The introduction of a suction catheter into the esophagus displaces the upper of the cuffs 15' slightly in order for the catheter tip to enter the esophagus. At such time, the pressure in the upper of the cuffs 15' protects the trachea from secretion contamination since it seals the opening 18' defined by the superglottic structure of the glottis.

Referring to FIGS. 5 and 9, it will be seen that the upper of the cuffs 15 or 15' need not be constructed in the doughnut-shape previously described. It is equally within the purview of the present invention for the upper of the cuffs 15 or 15' to be longitudinally elongated and adapted to conform to the cavity 19 or 19' defined by the wall 20 or 20' of the pharynx in a size greater than the opening 18 or 18' partially defined by the superglottic structure of the glottis. As long as the upper of the cuffs 15 or 15' meets this criteria, the precise shape is not critical although the shapes disclosed have been found to be advantageous.

Referring to FIG. 10, an additional alternative embodiment of cuffed endotracheal tube 10" is illustrated. The device 10" includes an elongated flexible air tube 11" having proximal and distal end portions 12" and 13", respectively, and a pair of enlargements 14" and 15" encircling the tube 11" intermediate the proximal and distal end portions 12" and 13". The lower of the enlargements 14" is sized and shaped to fall short of fully occupying the cavity defined by the wall of the trachea of a patient and rests at or below the opening defined by the lower lateral surfaces of the larynx. The upper of the enlargements 15" is sized and shaped to fully occupy the cavity defined by the wall of the pharynx of a patient and seals the opening defined by the superglottic structure of the glottis. The device 10" further includes the proximal end portion 25" of the lower of the enlargements 14" being spaced from the distal end portion 28" of the upper of the enlargements 15". As will be appreciated, the distance between the enlargements 14" and 15" can correspond to the distance between the enlargements 14 and 15 or, alternatively, the distance between the enlargements 14' and 15'.

In the embodiment illustrated in FIG. 10, the upper enlargement 15" is preferably an inelastic inflatable-deflatable cuff but the lower enlargement 14" is simply a bulbous segment in the flexible air tube 11' itself. The inflation means 21" will then comprise a single channel 23" within the wall of the tube 11" leading from the cuff 15" to the proximal end portion 12" of the tube 11" for syringe attachment. A cuff segment 29" intermediate the bulbous segment 14" and the cuff 15" and in communication with the cuff 15" can also be provided having a generally triangular configuration (as shown in FIG. 10 and similar to cuff segment 29 illustrated in FIGS. 5 and 6) under full inflation being sized and shaped to fully occupy and seal the opening defined by the glottis of a patient.

As will be appreciated, the bulbous segment 14" is not inflatable or deflatable. It is preferably formed of the same material as the tube 11" so as to have shape retaining characteristics. The bulbous segment 14", which is preferably integral with the tube 11", will therefore be sized and shaped in a manner so as to temporarily displace and enlarge the opening defined by the superglottic structure of the glottis, the vocal cords, and the lower lateral surfaces of the larynx during insertion. It will be appreciated that the bulbous segment 14" will cooperate with the cuff 15" thereafter to anchor the device 10" after insertion to prevent bronchial intubation or inadvertent extubation. At the same time, the bulbous segment 14" is sized and shaped so as to readily permit extubation as desired after deflating the cuff 15".

Figure 3:
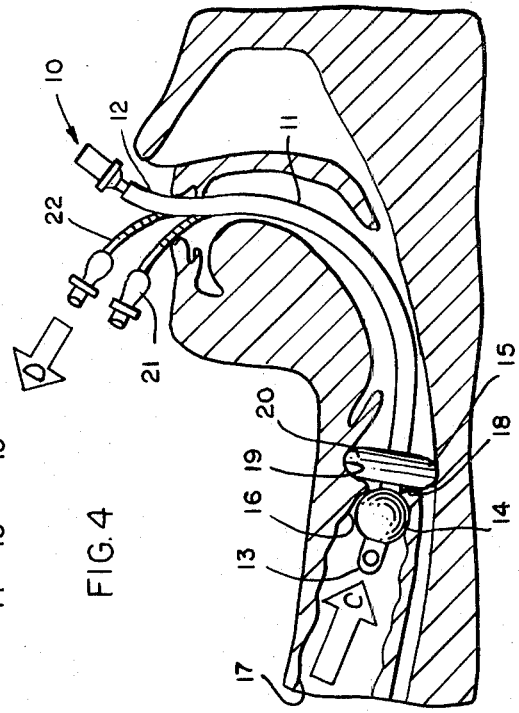
FIG. 3 is a view similar to FIG. 1 illustrating the first three steps of the method of using the cuffed endotracheal tube of the invention.
Figure 4:
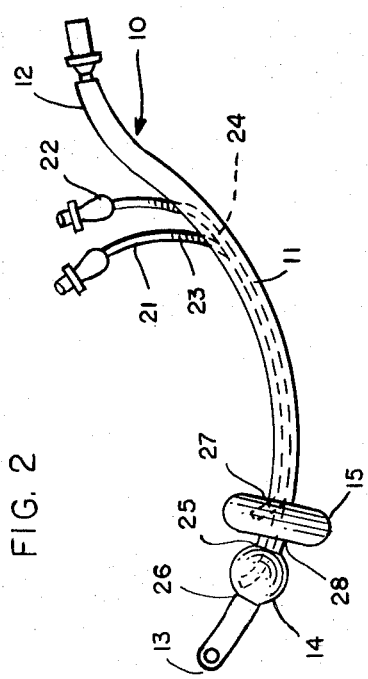
FIG. 4 is a view similar to FIG. 1 illustrating the last three steps of the method of using the cuffed endotracheal tube of the invention.

The method of using any of the cuffed endotracheal tubes 10, 10' or 10" of the type described can best be understood by considering a representative embodiment and referring to FIGS. 3 and 4. First, an elongated flexible air tube 11 is provided having proximal and distal end portions 12 and 13 wherein a pair of enlargements 14 and 15, at least the upper one of which is an inelastic inflatable-deflatable cuff, encircle the tube 11 intermediate the proximal and distal end portions 12 and 13 thereof. Second, the tube 11 is inserted through the mouth of a patient into the trachea to provide a passage for artificial respiration with the cuff 15 deflated until the lower enlargement 14 is positioned below the subglottic structure of the glottis. Third, the lower enlargement 14 is sized and shaped to fall short of fully occupying the cavity 16 defined by the wall 17 of the trachea but is sized greater than the opening 18 partially defined by the lower lateral surfaces of the larynx. Fourth, the tube 11 is withdrawn causing the lower enlargement 14 to move upwardly in the trachea until resistance is encountered indicating that the lower enlargement 14 is positioned against the opening 18 partially defined by the lower lateral surfaces of the larynx. Fifth, the cuff 15 is inflated to a size and shape fully occupying the cavity 19 defined by the wall 20 of the pharynx and to a size greater than the opening 18 partially defined by the superglottic structure of the glottis. Sixth, the tube 11 is moved toward insertion through the mouth of the patient further into the trachea with the cuff 15 inflated such that resistance indicates that the cuff 15 is properly anchored in the opening 18 partially defined by the glottis and the lower enlargement 14 rests at or below the opening 18 partially defined by the lower lateral surfaces of the larynx. With these features illustrated by the arrows A, B, C and D in FIGS. 3 and 4, the method provides a safe and effective way of assuring proper placement for any of the cuffed endotracheal tubes 10, 10' or 10" by providing a positive external indication by reason of the location of the enlargements on either side of the glottis.

It will be appreciated from the above description that the present invention overcomes the defects characteristically associated with conventional single cuffed endotracheal tubes as well as alternately inflated mid-tracheal double cuff structures of the prior art. These goals are accomplished with a unique structural combination and combination of steps in a device and method heretofore not available or known in the art. With the present invention, I have provided a safe and effective device and method which is at the same time capable of assuring proper placement in the trachea rather than the esophagus by providing a positive external indication by reason of the location of cuffs on either side of the glottis.

While in the foregoing specification a detailed description of the invention has been set forth for purposes of illustration, variations of the details herein given may be made by those skilled in the art without departing from the spirit and scope of the invention.

I claim:

1. A cuffed endotracheal tube adapted for insertion through the mouth of a patient to provide a passage for artificial respiration comprising:

an elongated flexible air tube having a proximal end portion adapted to be located external to the mouth and a distal end portion adapted to be located within the trachea;

anchoring means located on said tube at two separate points along said tube intermediate said proximal and distal end portions thereof, the lower of said means radially extending from said tube and adapted to contact the area of the trachea around and below the opening defined by the larynx without exerting pressure against the wall of the trachea, the upper of said means extending radially from said tube and adapted to contact the area around and above the opening defined by the larynx while also exerting pressure against the wall of the pharynx;

said elongated flexible air tube being positively anchored by the upper and lower of said means associated with said tube in a position in which the upper of said means provides a seal to prevent leakage of air during artificial respiration while at the same time preventing secretions from travelling into the area of the upper trachea or larynx.

2. The cuffed endotracheal tube of claim 1 wherein said anchoring means comprise a pair of inflatable-deflatable cuffs, and including separate means for inflating said cuffs, the upper of said cuffs sealing the opening partially defined by the superglottic structure of the glottis during use.

3. The cuffed endotracheal tube of claim 2 wherein said separate means for inflating said cuffs comprises separate and distinct channels within the wall of said tube leading from said cuffs to said proximal end portion of said tube for syringe attachment.

4. The cuffed endotracheal tube of claim 3 wherein said cuffs have proximal and distal end portions with said distal end portion of the upper of said cuffs being spaced from said proximal end portion of the lower of said cuffs.

5. The cuffed endotracheal tube of claim 4 including a cuffed segment intermediate the lower and upper of said cuffs and in communication with one of said cuffs, said cuff segment having a generally triangular configuration and being sized and shaped to fully occupy and seal the opening partially defined by the glottis during use.

6. The cuffed endotracheal tube of claim 2 wherein the upper of said cuffs is donut-shaped to seal against the soft tissues of the lower pharynx and the upper glottis to prevent secretions from travelling into the area of the upper trachea or larynx during use.

7. The cuffed endotracheal tube of claim 2 wherein the lower of said cuffs is spherical to approximate the semi-rigid structure of the lower glottis during use.

8. The cuffed endotracheal tube of claim 2 wherein the lower of said cuffs is of a size greater than the opening defined by the larynx to anchor said tube against inadvertent extubation during use.

9. The cuffed endotracheal tube of claim 2 wherein the lower of said cuffs is constructed of thick-walled polyvinylchloride and the upper of said cuffs is constructed of thin-walled polyvinylchloride.

* * * * *